United States Patent [19]

Danna et al.

[11] 4,261,368

[45] Apr. 14, 1981

[54] ELECTRONIC BLOOD PRESSURE DEVICE

[75] Inventors: Dominick Danna, Syracuse; Raymond A. Lia, Auburn, both of N.Y.

[73] Assignee: Welch Allyn, Inc., Skaneateles Falls, N.Y.

[21] Appl. No.: 32,143

[22] Filed: Apr. 23, 1979

[51] Int. Cl.$^3$ .............................................. A61B 5/02
[52] U.S. Cl. .................................................. 128/680
[58] Field of Search .................. 128/680-683

[56] References Cited

U.S. PATENT DOCUMENTS

| 3,308,811 | 3/1967 | Gillette et al. | 128/680 |
| 3,906,937 | 9/1975 | Arouson | 128/680 |
| 4,144,879 | 3/1979 | Nakayama et al. | 128/680 |
| 4,174,707 | 11/1979 | Link et al. | 128/681 |
| 4,181,122 | 1/1980 | Ueda | 128/680 |

FOREIGN PATENT DOCUMENTS 2628758  1/1978  Fed. Rep. of Germany ........... 128/680
2820379  3/1979  Fed. Rep. of Germany ........... 128/680

OTHER PUBLICATIONS

Schulze, A. E. et al., "A System for Autom. Meas. and Dig. Display of Sys/Dias. Blood Pressures" Southwestern IEEE Conf. Record Apr. 1968, pp. 17F1-17F5.

*Primary Examiner*—Francis J. Jaworski
*Attorney, Agent, or Firm*—Bruns & Jenney

[57] ABSTRACT

A blood pressure measuring and recording device that utilizes a piezoelectric crystal transducer for sensing the pressure of the blood in the brachial artery. The transducer is positioned in the cuff in an unrestricted manner whereby it in effect "floats". The cuff pressure and blood pressure coact to cause the crystal transducer to produce a waveform in which the relationship of the amplitudes of the positive and negative pulses indicate the systolic and diastolic pressures. Means are provided in the circuitry of the device for accurately distinguishing blood pressure pulses from spurious signals.

1 Claim, 3 Drawing Figures

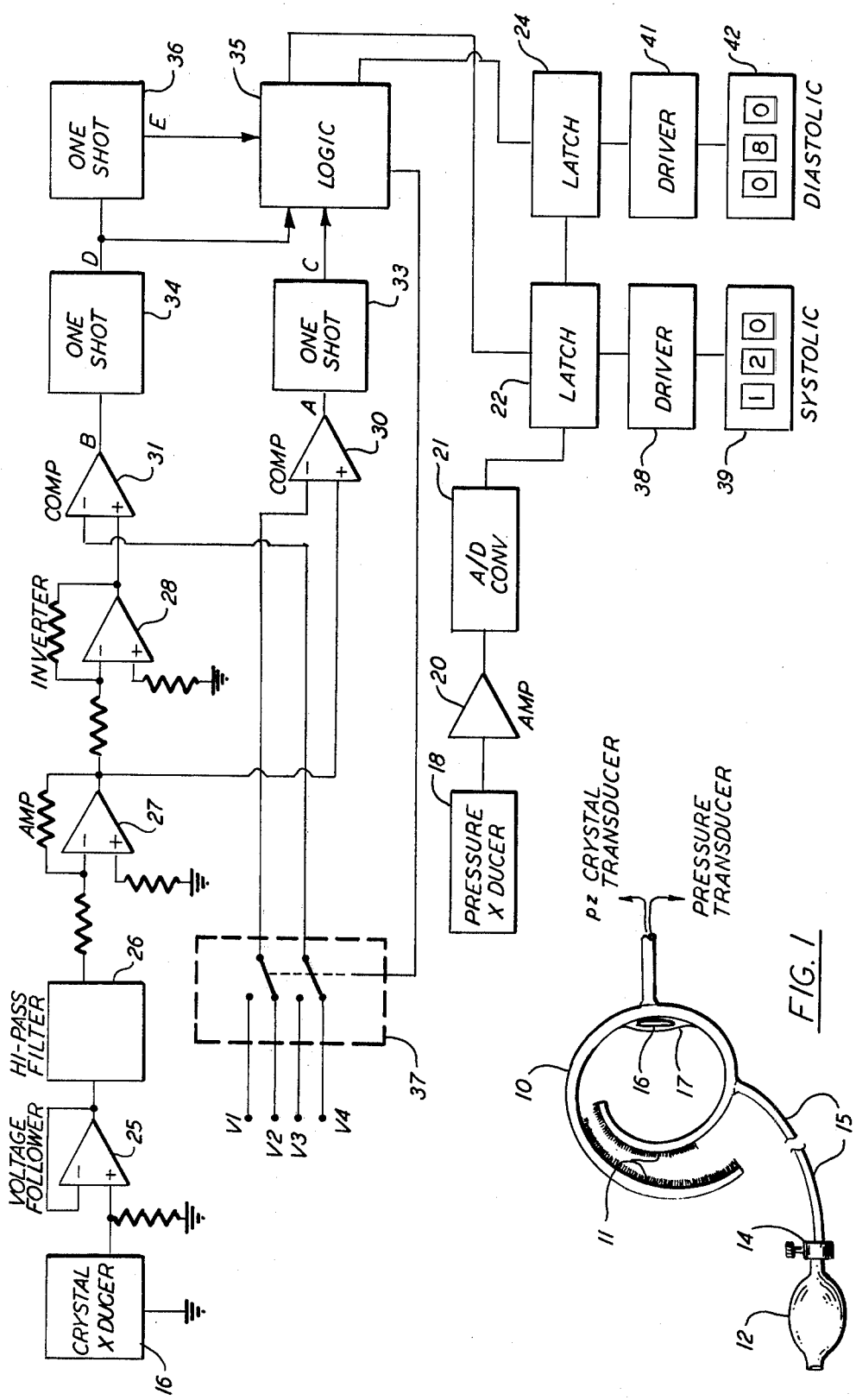

ELECTRONIC BLOOD PRESSURE DEVICE

BACKGROUND OF THE INVENTION

This invention relates generally to blood pressure measuring apparatus, and has particular reference to a novel electronic device that is capable of consistently measuring systolic and diastolic blood pressures with great accuracy.

Through the years, blood pressure has usually been measured by means of a standard pressure cuff and a stethoscope and the degree of accuracy of the measurement has depended to a great extent on the skill of the user of this equipment. More recently, a number of electronic blood pressure devices have been developed with the objective of producing accurate results even though operated by unskilled personnel. The sophisticated electronic devices are complex and relatively expensive and, unfortunately, quite frequently give erroneous readings caused by noise resulting from muscular movement or other spurious signals.

Electronic blood pressure devices are disclosed in U.S. Pat. Nos. 3,978,848 and 4,026,277 which represent the closest prior art known to the applicants. Neither of the devices disclosed by these patents utilizes a transducer that produces a waveform wherein the relationship of the amplitudes of the positive and negative pulses indicate the systolic and diastolic pressures. In addition to the foregoing, the following U.S. patents are considered by the applicants as being pertinent to the present invention: U.S. Pat. Nos. 3,930,494; 4,009,709; 4,011,860; 4,058,117; 4,074,711 and 4,078,551.

SUMMARY OF THE INVENTION

The electronic blood pressure device of the present invention is capable of accurately determining and recording systolic and diastolic pressures. This desired result is made possible in part through the utilization of a piezoelectric crystal transducer that is mounted in an unrestricted manner in a pocket in the cuff. The crystal transducer produces a waveform in which the relationship of the amplitudes of positive and negative pulses indicate the systolic and diastolic pressures.

In using the transducer waveform, the positive and negative pulses are separated and compared in comparators with predetermined voltage levels. The outputs of these comparators are used to determine the systolic and diastolic blood pressures by means of a logic algorithm. The device of the invention also includes means for accurately distinguishing blood pressure pulses from spurious signals of various kinds.

BRIEF DESCRIPTION OF THE DRAWINGS

FIG. 1 is a diagrammatic portrayal of a sphygmomanometer cuff forming a part of the present invention;

FIG. 2 is a symbolic block diagram of the blood pressure device of the present invention.

DESCRIPTION OF THE PREFERRED EMBODIMENT

Figure 3:
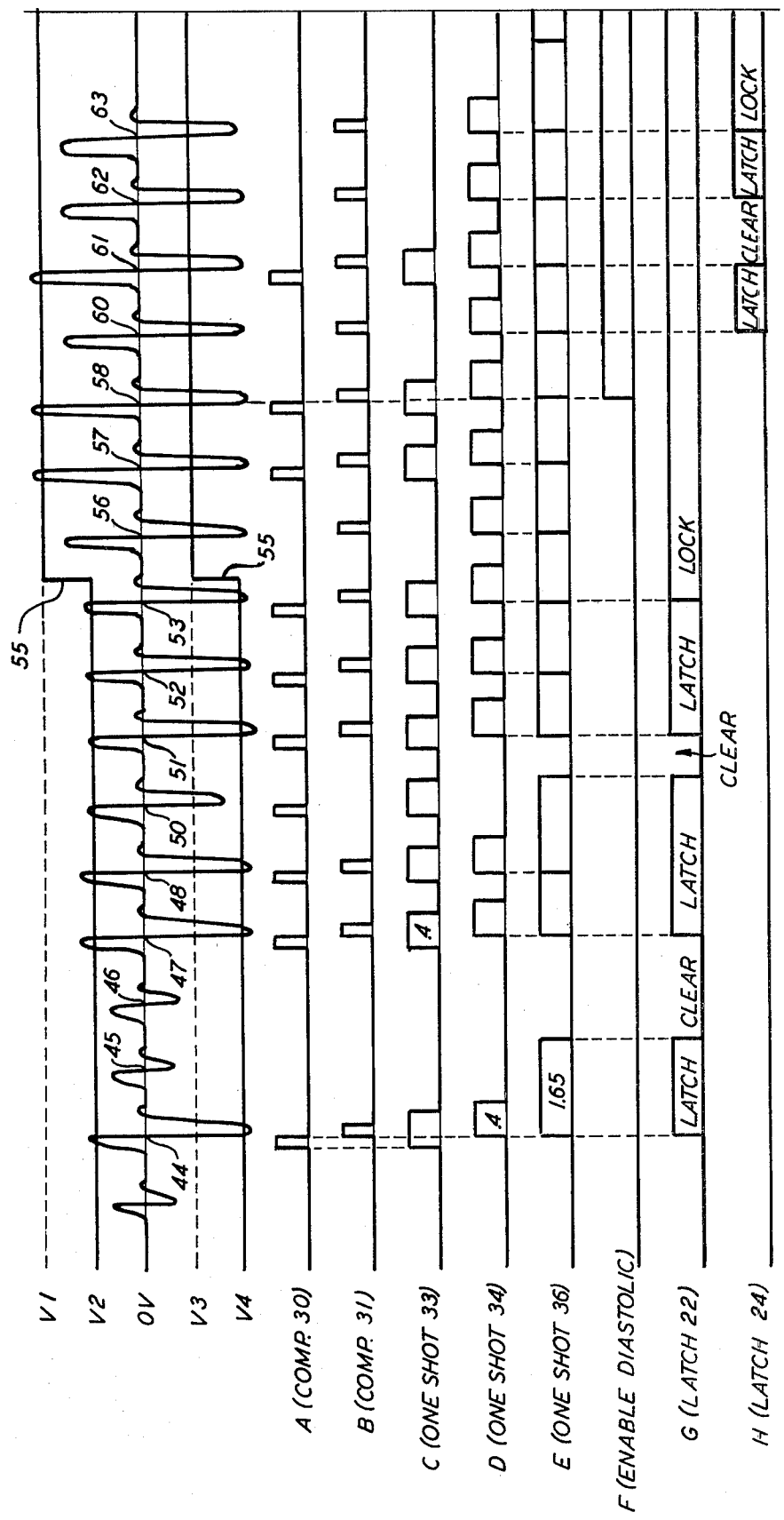
FIG. 3 is a timing diagram showing the operational sequence of the device of the invention in performing blood pressure measurements.

Having reference now to the drawings, FIG. 1 is a diagrammatic illustration of a sphygmomanometer cuff 10, the purpose of which is well known. The cuff can be secured in position on the arm by fastening means 11 commercially available under the trademark "VEL-CRO". The cuff can be inflated as by a bulb 12 that is connected to the interior of the cuff through a valve 14 and conduit 15.

In accord with the invention, a piezoelectric crystal in the form of a thin flat disc 16 is positioned in a pocket 17 in the cuff. Unlike the active element in a microphone, the crystal is not mounted in a restricted manner so that it in effect "floats" in the pocket. The fluid pressure in the cuff 10 and the blood pressure pulses or sphygmus signals operate to bend the crystal 16 in opposite directions thereby generating positive and negative voltages. Thus, a blood pressure pulse bends the crystal in one direction against the opposing force of the fluid pressure and when the pulse subsides the fluid pressure bends the crystal in the opposite direction.

In addition to the piezoelectric crystal 16, a conventional gage pressure transducer can be mounted in the cuff 10, or it can be located outside the cuff and operably connected to it. In any case, as indicated in FIG. 1, the two transducers produce output signals that are fed into the electronic portion of the device of the invention which portion is shown by the block diagram of FIG. 2

In FIG. 2, the pressure transducer is indicated at 18 and its output is connected to an amplifier 20 which in turn is connected to an analog to digital converter 21. The output of the converter is connected to a first latch means 22 and a second latch means 24, to be described in more detail hereinafter.

The crystal transducer 16, FIG. 2, is connected to a voltage follower 25 the output of which is connected to a high pass filter 26. The voltage follower matches the high impedance of the transducer to the low impedance of the high pass filter. The high pass filter 26 serves to eliminate body movement noise vibrations which are less than a certain predetermined frequency level.

The output of high pass filter 26 is connected to an amplifier 27 and the output of the latter is connected to an inverter 28 and also to one input of a first comparator 30. The output of the inverter is connected to one input of a second comparator 31. The other input of each comparator is connected to a voltage source to be described. The outputs of the first and second comparators 30 and 31 are respectively connected to monostable multivibrators 33,34 also referred to herein as one-shots. The one-shots 33 and 34 are non-retriggerable and each has a period or pulse duration of approximately 0.4 second.

The output of one-shot 33 is connected to an input of a logic block 35 which provides various logic decisions as will be seen. The output of one-shot 34 is connected to another input of the logic block 35 and also to a retriggerable one-shot 36 having a normal pulse duration of approximately 1.65 second. The output of one-shot 36 is connected to a third input of the logic block 35.

The logic block 35 has three outputs two of which are respectively connected to the latch means 22 and 24. The third logic block output is connected to a voltage switching means 37 to be described. The latch means 22 is connected through a driver 38 to a digital display 39 for the systolic blood pressure, and latch means 24 is connected through a driver 41 to a digital display 42 for the diastolic blood pressure.

The operation of the blood pressure device is as follows, FIGS. 2 and 3. In FIG. 3, the waveform generated by the crystal transducer 16 is shown at the top. This waveform occurs over a period of time during which the cuff pressure, which is initially raised to a point well above normal maximum blood pressure, is gradually decreased at a substantially constant rate. In accord with the invention, both positive and negative voltage pulses are utilized, and the pulse amplitudes are measured against or compared with known voltage levels. In determining systolic blood pressure, the positive pulse is compared with voltage V2 and the negative pulse with voltage V4. In determining diastolic blood pressure, another set of voltages is employed, the positive pulse being compared with voltage V1 and the negative pulse with voltage V3.

When a positive pulse exceeds voltage V2, it triggers comparator 30 and produces a pulse as shown on line A, FIG. 3. Similarly, when a negative pulse exceeds voltage V4, it triggers comparator 31 and produces a pulse as shown on line B. The comparator pulses A and B then trigger the non-retriggerable one-shots 33 and 34, respectively, and the latter produce pulses of approximately 0.4 second duration as indicated on lines C and D, FIG. 3. The leading edges of the positive and negative waveform pulses respectively produce the 0.4 second pulses. The 0.4 second pulses provide deadbands that prevent anything but these leading edges from entering the logic.

The output of comparator 31, pulse B, also triggers the retriggerable one-shot 36 which produces a pulse of approximately 1.65 seconds duration as indicated on line E. The one-shot 36 pulse E enables counters in the logic block 35. The logic must receive three sets of C,D pulses, the second and third sets occurring within 1.65 seconds of the set immediately preceding, for the systolic digital reading to be locked in. The cuff pressure appearing at the time of the first set of C,D pulses is the reading that is locked in. If fewer pulses appear within the permissible time frame, the one-shot 36 resets the counters. This arrangement helps the device to distinguish blood pressure pulses from artifact motion signals.

With further reference to FIG. 3, it can be seen that in the waveform, wave 44 is the first wave wherein the positive pulse exceeds voltage level V2 and the negative pulse exceeds voltage level V4. This, as described above, causes pulses A, B, C, D and E to be produced and also causes the latch 22 to latch or hold the reading on the digital display 39. The displays 39 and 42 initially show the relatively high pressure to which the cuff has been raised and then as the air is allowed to bleed out of the cuff the display readings steadily decrease, the pressure in the cuff being sensed by the transducer 18. The reading for the systolic display 39 is latched as indicated on line G of FIG. 3 when the latch 22 receives a signal from logic block 35. The signal from the logic block is occasioned by the entry into the block of pulse C followed, within the duration of pulse C, by the entry of pulse D, FIGS. 2 and 3.

Still referring to the waveform of FIG. 3, it can be seen that following wave 44 there are two waves 45 and 46 in which the positive pulses do not exceed voltage V2 and the negative pulses do not exceed voltage V4. This being the case, pulses A, B, C and D are not generated, and since a second set of C,D pulses is not received by the logic block within the 1.65 second time period of one-shot 36 the latter returns to its stable state at the end of the period as shown on line E, FIG. 3. When the one-shot 36 returns to its stable state, the counters in the logic block are reset and latch 22 is cleared causing resumption of the downward reading in the display 39.

Following waves 45,46 described above, there appear in the waveform two waves 47 and 48 in which the positive pulses exceed voltage V2 and the negative pulses exceed voltage V4. Since wave 47 satisfies these conditions, it causes pulses A, B, C, D and E to be produced as described above and the entry of the C,D pulses substantially simultaneously into the logic block 35 again enables the counters therein and latches the systolic display 39 as indicated on line G, FIG. 3. The succeeding wave 48 also causes pulses A, B, C, D and E to be produced and, because a second set of C,D pulses enters the logic block within the 1.65 second time period of one-shot 36, the latter is retriggered as shown on line E and starts a new 1.65 second pulse. Because of this, the display 39 remains latched. Following wave 48, a wave 50 appears in which the positive pulse exceeds voltage V2 but the negative pulse does not exceed voltage V4. The positive pulse of the wave produces pulses A and C but pulses B and D are not produced by the negative pulse. As a result, a third set of C,D pulses is not received by the logic block within the 1.65 second period of one-shot 36, and at the end of the period the one-shot returns to its stable state as indicated on line E. This also resets the counters in the logic block and clears latch 22 whereupon the downward readings in display 39 resume.

After wave 50, three waves 51, 52 and 53 appear in the waveform and in each of these waves the positive pulse exceeds voltage V2 and the negative pulse exceeds voltage V4. As a result, three sets of C,D pulses are received by the logic block, the receipt of the first D pulse enabling the logic counters and operating through latch 22 to again latch the systolic display 39. In this series of waves, the logic block receives the second and third sets of C,D pulses within 1.65 seconds of the first and second sets, respectively, and the receipt of the three sets of pulses within the prescribed time frame is observed by the counters. The recording of the three sets of pulses by the counters causes the previously latched display 39 to be locked and triggers the voltage switching means 37 whereby comparison voltages V1 and V3 are fed into comparators 30 and 31, respectively. This shift in comparative voltages is indicated at 55 in FIG. 3.

Upon locking the systolic display 39 and shifting the voltages, the device of the invention is ready to determine the diastolic blood pressure. First, however, the logic block must be enabled for diastolic and this occurs when the logic block receives two sets of C,D pulses. Thereafter, for the diastolic display to be locked requires two consecutive waveform waves in which the positive pulse does not exceed voltage V1 and the negative pulse exceeds voltage V3.

In the waveform, FIG. 3, the first wave 56 to appear after the voltage shift has a positive pulse that does not exceed voltage V1 and a negative pulse that exceeds voltage V3. Wave 56 thus satisfies the conditions for latching the diastolic display 42 but this cannot happen because there has not yet been a diastolic enable in the logic. For wave 56, pulses A and C are not produced; pulses B and D are produced.

Following wave 56, there are two waves 57 and 58 each of which has a positive pulse that exceeds voltage V1 and a negative pulse that exceeds voltage V3. Each wave therefore produces pulses A, B, C, D and E and, since the logic block receives two sets of C,D pulses, there is a diastolic enable in the logic as indicated on line F, FIG. 3. After wave 58, wave 60 appears with a positive pulse that does not exceed voltage V1 and a negative pulse that exceeds V3. This produces pulses B, D and E and satisfies the condition for latching the diastolic display 42, i.e. that the logic block receive a D pulse only. This diastolic latch is indicated on line H, FIG. 3, and operates to latch or hold the reading on the digital display 42.

In the next wave 61 to appear after wave 60, both the positive and negative pulses exceed the comparison voltages causing pulses A, B, C, D and E to be produced. This is not what is required to latch or lock the diastolic display and therefore the latch 24 clears, line H, and the downward readings in display 42 resume. Following wave 61, there are two waves 62 and 63 each of which has a positive pulse that does not exceed voltage V1 and a negative pulse that exceeds voltage V3. Each wave therefore produces B, D and E pulses, and receipt by the logic block of the D pulse produced by wave 62 latches the display 42 and enables the logic counters. Receipt by the logic of a second D pulse, produced by wave 63, operates to lock the diastolic display completing the determination and recording of the patient's blood pressure.

From the foregoing description it will be apparent that the invention provides a novel blood pressure measuring and recording device that achieves accurate results without the need for operation by highly skilled personnel. By eliminating background acoustical noise as a variable factor, high accuracy is attainable. As will be understood by those familiar with the art, the invention may be embodied in other specific forms without departing from the spirit or essential characteristics thereof.

We claim:

1. In a blood pressure measuring and recording device: an inflatable cuff, a crystal transducer positioned in the cuff and responsive to blood pressure pulses and cuff pressure to produce a voltage waveform having positive and negative pulses, a gage pressure transducer operably connected to the cuff, a first digital display for systolic blood pressure and a second digital display for diastolic blood pressure, means including an analog to digital converter operably connecting the gage pressure transducer to the two digital displays, means including a first comparator for producing a first signal when the amplitudes of the positive voltage pulses reach a predetermined level, means including an inverter and a second comparator for producing a second signal when the amplitudes of the negative voltage pulses reach a predetermined level, and means responsive to the presence or absence of said first and second signals for determining and recording the patient's blood pressure, said last-named means including a voltage source having two sets of voltage levels, means operably connecting the voltage source with an input of each of the first and second comparators, one set of the voltages being fed into the comparators for determining systolic blood pressure and the other set of voltages being fed into the comparators for determining diastolic blood pressure, and means coacting with the voltage source for shifting from one set of voltages to the other.

* * * * *